(12) United States Patent
Deetsch

(10) Patent No.: US 11,523,927 B2
(45) Date of Patent: Dec. 13, 2022

(54) HEAD AND NECK SUPPORT APPARATUS

(71) Applicant: Todd Douglas Deetsch, Louisville, KY (US)

(72) Inventor: Todd Douglas Deetsch, Louisville, KY (US)

(*) Notice: Subject to any disclaimer, the term of this patent is extended or adjusted under 35 U.S.C. 154(b) by 355 days.

(21) Appl. No.: 15/999,184

(22) Filed: Aug. 17, 2018

(65) Prior Publication Data

US 2020/0054475 A1 Feb. 20, 2020

(51) Int. Cl.
*A61F 5/055* (2006.01)

(52) U.S. Cl.
CPC .................. *A61F 5/055* (2013.01)

(58) Field of Classification Search
CPC ........ A61F 5/055; A61F 5/05883; A61F 5/02; A61F 5/022; A61F 5/024; A61F 5/026; A61F 5/028; A61F 5/3707; A61F 5/3792; A61F 5/05891; A47C 16/00; A47C 31/00; A47C 7/02; A47C 7/425; A47C 7/46; A47G 9/10; Y10S 128/23; A41D 13/00; A41D 13/0531; A61G 13/121; A61G 13/1215; A61G 7/07; A61G 7/072
USPC .......... 602/5, 17–19; 128/23, 845, 846, 869, 128/875, 876; 297/284.5, 254, 283, 231, 297/255, 256; 5/640, 622; 601/39
See application file for complete search history.

(56) References Cited

U.S. PATENT DOCUMENTS

| | | | |
|---|---|---|---|
| 15,581 A | 8/1856 | Slaughter | |
| 16,300 A | 12/1856 | Wilson | |
| 72,467 A | 12/1867 | Dunlap | |
| 138,463 A | 4/1873 | Wright | |
| 357,915 A * | 2/1887 | Ferry | A47C 7/383 297/393 |
| 382,949 A | 5/1888 | Campbell | |
| 392,212 A | 11/1888 | McCollum | |
| 1,463,081 A | 7/1923 | Hancock | |
| 2,088,207 A | 7/1935 | Kaiser | |
| 2,223,276 A | 12/1937 | Ward | |
| 3,657,739 A | 4/1972 | Holmes, Sr. | |
| 4,870,705 A | 10/1989 | Higby et al. | |

(Continued)

FOREIGN PATENT DOCUMENTS

| | | | | |
|---|---|---|---|---|
| DE | 20 2015008090 U1 | 12/2015 | | |
| DE | 202015008090 U1 * | 12/2015 | ............. | A47C 7/425 |

(Continued)

OTHER PUBLICATIONS

Translation of DE-202015008090-U1 (Year: 2015).*
Translation of JP-2015132034-A (Year: 2015).*

*Primary Examiner* — Alireza Nia
*Assistant Examiner* — Daniel A Miller

(57) ABSTRACT

A neck support apparatus has a frame with a pair of risers spaced apart from each other and each having a bottom end and a top end. The frame is positioned on the back of a wearer. A harness maintains the frame in position. A flexible panel spans between the two risers. The shape of the two risers, the initial tautness of the flexible panel, and the material of the flexible panel, and other factors, contribute to the shape of the support surface that the flexible surface presents to the head and neck of a wearer of the apparatus. The flexible panel provides support to the head and neck of a wearer when the head of the wearer is tilted back, such as when a person is doing overhead work.

9 Claims, 12 Drawing Sheets

(56) References Cited

U.S. PATENT DOCUMENTS

| | | | |
|---|---|---|---|
| 5,190,347 A * | 3/1993 | Shiow-Lan | A47C 7/425 297/230.11 |
| 5,409,450 A | 4/1995 | Donelson | |
| 5,483,698 A | 1/1996 | Douglas, Jr. | |
| 5,551,081 A * | 9/1996 | Starnes | A41D 13/0512 2/468 |
| 5,637,067 A | 6/1997 | Ausmus | |
| 5,738,640 A | 4/1998 | Carlson-Orsi | |
| 5,840,051 A * | 11/1998 | Towsley | A61F 5/0125 602/19 |
| 6,039,708 A | 3/2000 | Schaming | |
| 6,135,973 A * | 10/2000 | Zapletal | A61F 5/3792 602/18 |
| 6,213,967 B1 | 4/2001 | Zapletal | |
| 6,308,345 B1 | 10/2001 | Williams, Jr. | |
| 6,409,694 B1 * | 6/2002 | Bugarin | A61F 5/055 128/DIG. 23 |
| 6,648,191 B2 * | 11/2003 | Giggleman | A45F 3/14 224/254 |
| 6,957,462 B1 * | 10/2005 | Wilcox | A47C 7/383 297/393 |
| 7,025,424 B2 * | 4/2006 | Harley | A47C 31/02 297/219.1 |
| 7,197,781 B2 | 4/2007 | Ramsbottom et al. | |
| 7,618,385 B2 | 11/2009 | Poole | |
| 7,865,987 B2 | 1/2011 | Deetsch | |
| 7,892,193 B2 | 2/2011 | Marchetto | |
| 7,901,327 B2 | 3/2011 | Hargis | |
| 9,332,795 B1 | 5/2016 | Jung | |
| D762,400 S | 8/2016 | Wong | |
| 9,427,652 B2 | 8/2016 | Khademi | |
| 9,526,360 B2 | 12/2016 | Sternlight et al. | |
| 9,635,962 B2 | 5/2017 | Sternlight et al. | |
| D790,880 S | 7/2017 | Wong et al. | |
| D790,881 S | 7/2017 | Wong | |
| D809,966 S | 2/2018 | Wong | |
| 2003/0050582 A1 | 3/2003 | Poole | |
| 2005/0102758 A1 * | 5/2005 | Ramsbottom | A61F 5/055 5/636 |
| 2005/0283884 A1 * | 12/2005 | Poole | A41D 13/05 2/410 |
| 2008/0201831 A1 | 8/2008 | Ronco | |
| 2008/0251084 A1 * | 10/2008 | Marchetto | A61F 5/055 602/17 |
| 2008/0271249 A1 * | 11/2008 | Deetsch | A47C 16/00 602/17 |
| 2011/0225736 A1 * | 9/2011 | Schwingendorf | B60N 2/882 5/652 |
| 2013/0061856 A1 * | 3/2013 | Khademi | A61F 13/128 128/845 |
| 2020/0188159 A1 * | 6/2020 | Hatch | A61F 5/028 |

FOREIGN PATENT DOCUMENTS

| | | | |
|---|---|---|---|
| JP | 2015132034 A * | 7/2015 | |
| JP | 2015132034 A | 7/2015 | |
| KR | 101168893 B1 | 8/2011 | |

* cited by examiner

HEAD AND NECK SUPPORT APPARATUS

FIELD OF THE INVENTION

This invention relates to the support of a person's neck or head. More specifically, this invention relates to an apparatus worn by a person to support the wearer's head or neck while performing overhead tasks such as work.

BACKGROUND OF THE INVENTION

There are a wide range of activities during which individuals perform tasks overhead, often while standing. Manufacturing assembly, repair, industrial inspection, lighting installation and repair, and ceiling installation, finishing, and repair are among the many work environments where it is common for workers to perform tasks overhead for extended periods of time. Frequently, the workers are standing while performing the tasks and may even walk from location to location while performing the various required tasks. This results in the workers having to look up continuously as they work, which means workers have to crane their head back for extended periods of time. This is, at the least, very fatiguing and may result in injuries in the long run, especially, if the worker needs to move their head from side to side while looking up.

RELEVANT ART

U.S. Pat. No. 7,892,193 by Marchetto is for an "OVERHEAD ACTIVITY HEAD-AND-NECK SUPPORT COLLAR". In Marchetto, a head-and-neck support collar is provided that supports the cervical region of the spine and the base of the skull when the head is in a tilted-back position. The collar is designed to reduce head-and-neck stress, strain and pain during physical activities that require the wearer to look upwards, especially for extended periods of time. The collar includes an elongated neck cushion that is positioned behind the neck of the user. A harness is attached to either end of the elongated neck cushion and is routed over the shoulders, under the arms and across the back. A two part quick release mechanism is provided between the harness and each end of the cushion to facilitate quick and complete release of the cushion from the harness. This quick release mechanism is preferably a hook and loop type fastener.

U.S. Patent by Bugarin is for a "NECK BRACE". Bugarin discloses a ventilated neck brace that provides support to the wearer's neck while providing improved ventilation and breathability. Most embodiments of the neck brace include an elongate member that defines a neck support, a transition section, and an elongated shoulder rest. Most configurations of the neck brace allow the wearer to adjust the width and length of the neck brace.

U.S. Pat. No. 7,865,987 by Deetsch is for a "HEAD POSITIONING APPARATUS". In Deetsch, a head positioning apparatus and method comprises a support member, at least one strap, and a ring. The support member can be adjustably located proximate to a user's head, neck, or other body parts, in order to limit movement of those body parts during activity. The apparatus and the disclosed methods may comprise additional elements, for example: additional straps; means of fastening said straps to an attachment point; one or more cushions slidably affixed to said straps; one or more buckles; and means to adjust tension.

U.S. Pat. No. 7,197,781 by Ramsbottom et al is for a "NECK SUPPORT". Ramsbottom is directed to a neck support comprising: a top portion for receiving a user's head; a bottom portion having a pair of wings for resting on shoulders of said user; and a middle portion, connecting said top portion to said bottom portion. The top and middle portions are made of a compressive mould material having memory characteristics. A harness keeps the top, bottom, and middle portion of the neck support in position.

U.S. Pat. No. 7,618,385 by Poole is for a "HEAD SUPPORT". The invention in Poole relates to head or neck supports which support the head or neck in a tilted back position. The neck support of Poole comprises or includes: a) a harness locatable to the upper body portions of a person, and b) a rigid member extending from a region of the harness stabilized in respect of and by the use of the harness relative to the body. When the neck support is in use, the harness is attached to the body of a person, the rigid member extending therefrom to provide a support area. When a person wearing the support is in a substantially upright position, and the head is tilted backwards to allow viewing of an object above the horizontal, the support area comes into contact with at least part of the back of the wearer's head and provides at least vertical support to the head.

In considering the relevant art, there is still a need for a device that provides support for the head and neck of a wearer performing overhead tasks where the device provides support through a range of motion without being restrictive and without requiring active effort by the wearer to displace the support device.

SUMMARY FOR EMBODIMENTS OF THE INVENTION

The several embodiments of the device, or apparatus, of the present invention provide support to the neck and/or head of a person wearing the apparatus while the person is performing overhead tasks. The device provides support without restricting the motion of the wearer and does not force the wearer to "fight against" the device. Support for the wearer is maintained throughout lateral motion ranges as well as when the wearer is looking directly upward.

As stated above, a user wears the apparatus. The several embodiments of the apparatus comprise a frame which supports a flexible panel. Generally, the frame contacts the wearer's back, and the flexible panel contacts the wearer's head, and that provides support to the head and neck of the wearer when the head is laid back into the flexible panel. In some embodiments, or in some positions, the flexible panel may also contact the wearer's neck, and additional support may be provided in that fashion. A harness connects to the frame. The harness is how a user wears the device, and it is the harness that maintains the frame in the appropriate position on the back of the wearer.

The frame comprises two risers spaced apart from each other with the flexible panel spanning between the two risers. The flexible panel is in tension as it spans between the risers. The flexible panel is made from a flexible material. The flexible material of the flexible panel may be referred to generically as cloth or fabric, but may be made of any suitable flexible material. For example, the flexible material may be a synthetic material not technically classified as cloth or fabric. In some embodiments of the device, the shape of the risers defines the contours of the flexible panel, such that when the wearer's head is laid back, the flexible panel cradles the head without restricting, or resisting, its movement. The curvature of the risers, the flexibility or elasticity of the flexible material, the tautness of the flexible material, the spacing of the risers, and other factors determine the shape and behavior of the flexible panel.

In some embodiments, the frame may have elements in addition to the risers. In embodiments where the risers are not directly joined together, additional frame elements may maintain the spacing of the risers. In some embodiments, a transverse frame member may connect the risers beneath the flexible panel to maintain the spacing of the risers. In embodiments where the flexible panel also connects to this transverse member below the flexible panel, this lower transverse member can also partially define the contour of the flexible panel. In some embodiments, a transverse frame member may connect the risers above the flexible panel to maintain the spacing of the risers. In embodiments where the flexible panel also connects to this transverse member above the flexible panel, this upper transverse member can also partially define the contour of the flexible panel. In some embodiments, the flexible panel may be formed by a sleeve that fits over the frame. In those embodiments, the sleeve envelopes the frame and a portion of the sleeve forms the flexible panel that contacts a wearer's head and sometimes neck.

In some embodiments, the frame may be a unitary hoop. This hoop may be opened or closed. In embodiments where the hoop is open, the risers are connected by a transverse member sufficiently stiff to maintain the risers in spaced apart position. In some embodiments with an open hoop frame, only the risers shape the flexible panel, and in other embodiments, the risers and transverse member contribute to the shape of the contour of the flexible panel. In embodiments with a closed hoop, two transverse elements maintain the risers in the spaced apart position. In embodiments where the flexible panel attaches to the upper and/or lower transverse elements, the transverse elements will contribute to the shape and behavior of the flexible panel.

In some embodiments, the risers may transition smoothly into the transverse elements. This is particularly the case in embodiments employing unitary construction, such as with the unitary construction of the open or closed hoops. In embodiments where the risers are curved, the curvature of the risers may blend into the curvature of the transverse member, or members. Additionally, the curvature of risers and transverse members may be defined within a plane, or may be non-planar. Frames with multiple curvatures of the risers and or transverse members can produce flexible panels which are somewhat taut but have complex curvatures. This allows the forming of a flexible panel that provides a contoured surface for a head to "roll" on which is also flexible and giving. This gives the wearer's head support in a wide range of positions, allowing fluid motion of the head, without the wearer experiencing resistance or having to "fight" the apparatus.

In the various embodiments, the flexible panel may attach to the frame in various manners and along various lengths of its perimeter. For example, the flexible panel may attach to the frame along the flexible panel's entire perimeter by wrapping around the frame and attaching to itself or it may attach directly to the frame along its entire perimeter by being glued to the frame, heat bonded, stitched to the frame, etc. Similarly, the perimeter of the flexible panel may have several sides with two of them generally opposing each other. The flexible panel may be attached to the frame at its opposing sides by wrapping around the frame and attaching to the interior of the flexible panel or by attaching directly to the frame. As mentioned above, the flexible panel may have be a portion of a sleeve that fits over the frame.

The harness that connects to the frame and maintains the frame in the appropriate location can take many forms. The form of the harness of an embodiment may depend on the particular configuration of the frame of an embodiment. In some embodiments, the harness may resemble the shoulder straps of a backpack and the device can be worn independent of whatever garments a wearer has on. In other embodiments, the harness connects to the clothing of the wearer. Straps of the harness may utilize several types of connectors to attach to the clothing of the wearer. Examples of connectors include: clamps that clamp onto fabric of the wearer's clothing; button holes to receive buttons on the wearer's clothing; loops that interact with the belt, or belt loops, of a wearer; buttons and clasps engaging a wearer's clothing; or any of the many ways a strap attaches to clothing. As with many typical harnesses, there are various ways in which the harness can be adjusted. Additionally, there are many ways by which the harness may attach to a frame. These include glue, heat bonding, wrapping, stitching, loops, clamps, etc. In some embodiments, the harness may attach to the frame indirectly by attaching to the flexible panel.

BRIEF DESCRIPTION OF THE DRAWINGS

Additional utility and features of the invention will become more fully apparent to those skilled in the art by reference to the following drawings, which illustrate some of the primary features of preferred embodiments.

DETAILED DESCRIPTION OF EMBODIMENTS

Figure 1:
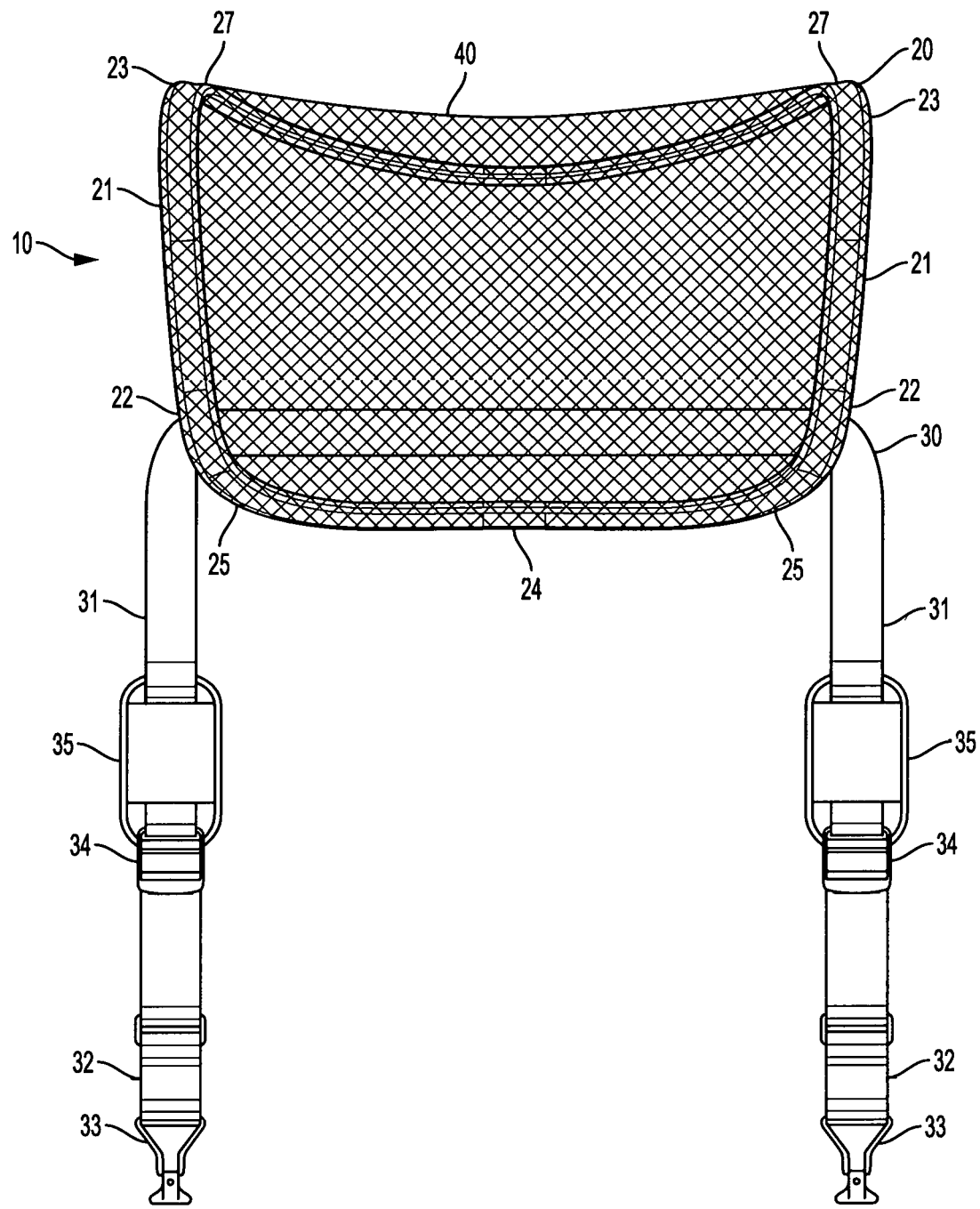
FIG. 1 is a front view of an embodiment of a neck support apparatus.

FIG. 1 is a front view of an embodiment of a neck support apparatus 10. In the embodiment shown in FIG. 1, neck support apparatus 10 has a frame 20, harness 30, and a panel 40 of flexible material fitted to frame 20. Harness 30 attaches to frame 20 and provides the means of attaching neck support apparatus 10 to a person, or to clothes that a person is wearing. A portion of frame 20 contacts a wearer's back, while panel 40 contacts a wearer's head, and or neck, when the head is tilted back.

In the embodiment shown in FIG. 1, frame 20 has a pair of risers 21 spaced a distance apart from each other and running generally up and down. Panel 40 spans between risers 21. Risers 21 each have a lower end 22 and an upper end 23. A lower transverse section 24 has two ends 25, each of which join a respective lower end 22 of a riser 21. Similarly, an upper transverse section 26 has two ends 27, each of which join a respective upper end 23 of a riser 21. In the embodiment of FIG. 1, lower transverse section 24 and upper transverse section 26 maintain risers 21 spaced apart.

Figure 2:
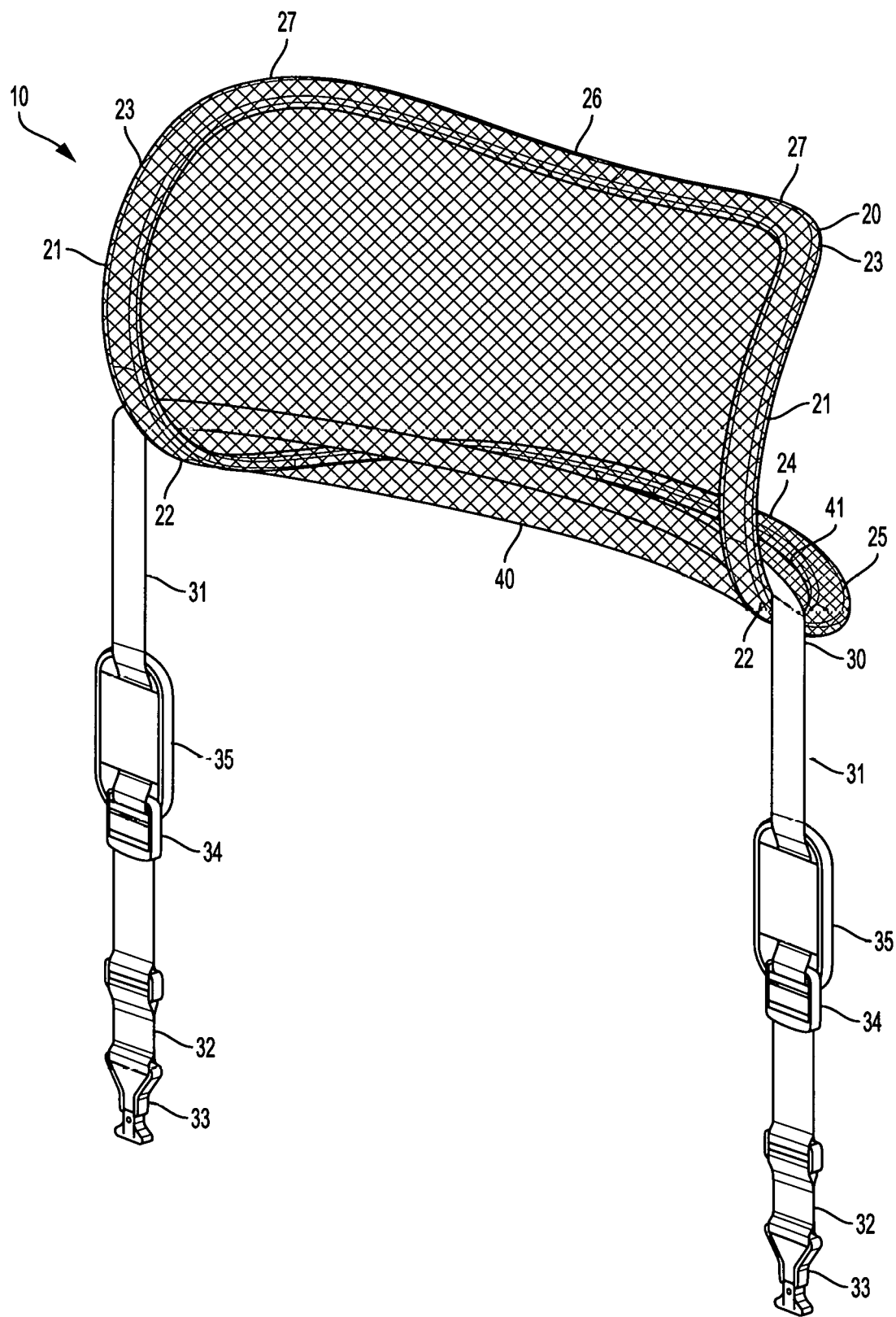
FIG. 2 is a right perspective view of an embodiment of a neck support apparatus.
Figure 3:
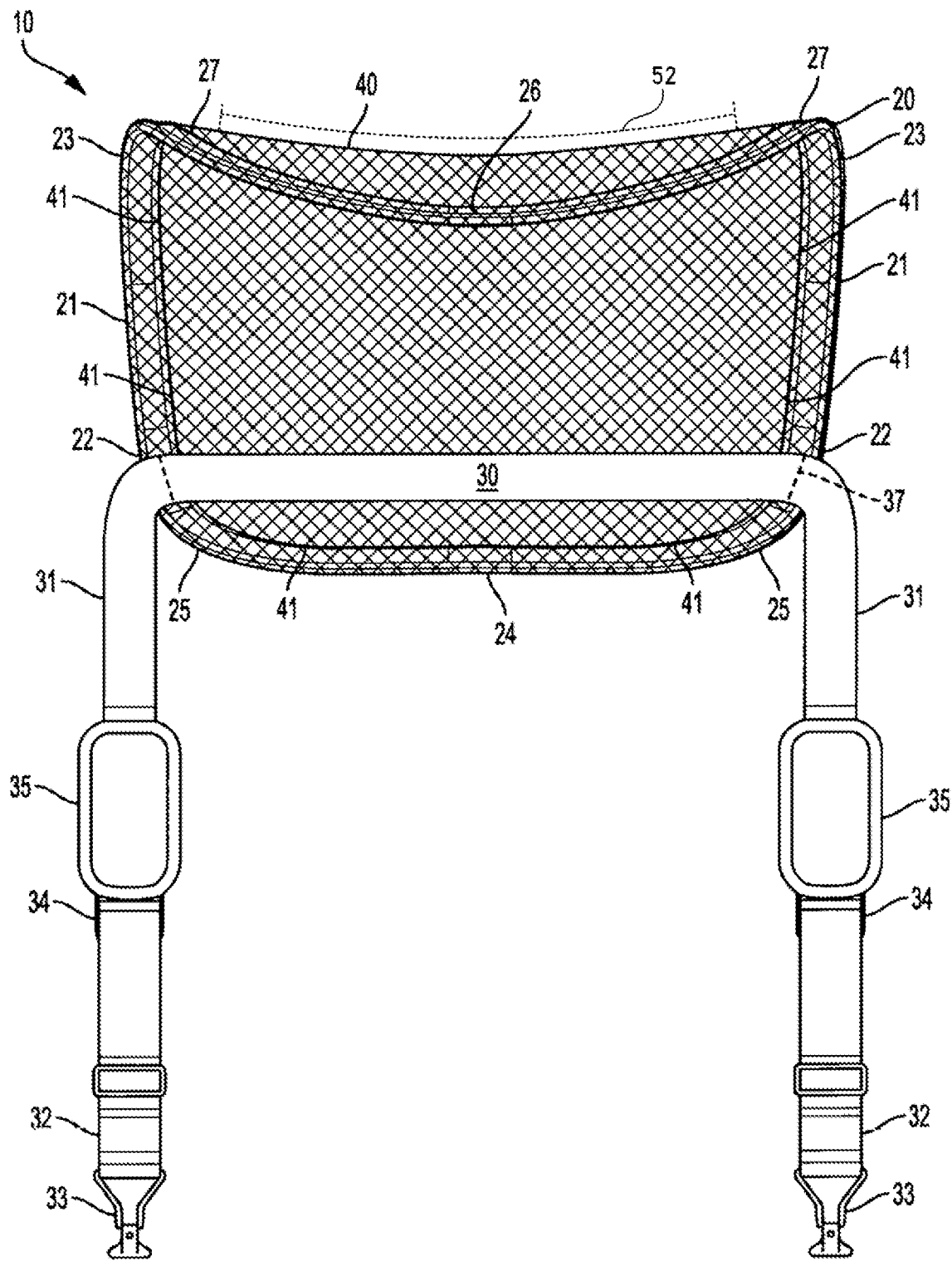
FIG. 3 is a back view of an embodiment of a neck support apparatus.

FIGS. 2 and 3 show additional views of an embodiment of a neck support apparatus 10 which provide additional visibility to the shape of frame 20, flexible panel 40, and how harness 30 works with frame 20. FIG. 2 is a right perspective view of an embodiment of neck support apparatus 10. FIG. 3 is a back view of an embodiment of neck support apparatus 10. In the embodiment shown in FIGS. 1, 2 and 3, harness 30 is comprised of a single strap 31 having two ends 32 and attached to frame 20 at two places. Each end 32 of strap 31 has a clamp 33 which is used to clamp onto the clothes of a wearer, such as a belt or the waist of trousers. The single strap 31 configuration of harness 30 allows harness 30 to maintain frame 20 in contact with a wearer's back while keeping the resulting tension within strap 31. This avoids requiring frame 20 to maintain its shape against the tug of harness 30 and allows frame 20 to have only the strength required to support the head and neck via panel 40. The tension in strap 31 may even assist frame 20 to resist drawing inwardly as panel 40 is loaded. Strap 31 may be adjustable to each side of frame 20 and may even have extensions which join to strap 31 while maintaining the functionality of a single strap 31. Alternatively, buckles 34 can loop strap 31 for adjustable length. Pads 35 of strap 31 distribute the tension of strap 31 as it passes over the shoulders 38 of the wearer. Any appropriate fastening 37 may be used to fasten strap 31 to frame 20. Fastening 37 may be stitching, glue, staples, screws, etc.

Other more complex harnesses or strap systems may be used. For example, some occupations may require the wearing of more extensive uniforms or equipment. Different embodiments of neck supporting apparatus 10 could employ different embodiments of harnesses 30 to accommodate the particular needs of an occupation. In some cases, the given apparel of an occupation may provide addition locations where a harness could attach.

Panel 40 spans between risers 21, exhibiting a first curvature 52, and may be thought of as creating a hammock or sling. However, panel 40 may maintain a more taut state than is usually associated with a sling or hammock. In the embodiment shown in FIG. 1, panel 40 has a perimeter 41 defining its extent and panel 40 is attached to frame 20 around the entirety of perimeter 41. Panel 40 is made of a flexible material such as cloth, mesh, various plastic based fabrics, etc. In some embodiments panel 40 may even be comprised of a foam material. Factors that determine the shape of the surface presented by panel 40 and how it interacts with the head and neck of a wearer of neck support apparatus 10 include: the elasticity of the flexible material; shape of frame 20; resilience of frame 20; where panel 40 attaches to frame 20; initial tautness of panel 40; as well as other factors.

For occupations surrounded by fire and electrical hazards, neck support apparatus 10 may be constructed from materials specially selected for those environments. Flexible panel 40 and harness 30 may be made from material that is arc-rated and/or self-extinguishing. An example of self-extinguishing material is Nomex® material produced by DuPont. Some materials may be reduced to ash when exposed to high voltage without producing flames. Frame 20 similarly may be constructed from a non-conductive material to mitigate shock hazards. All of neck support apparatus 10 may be constructed from suitable flame retardant materials having the needed material characteristics for a given elements function. For example, frame 20 may be constructed from flame retardant material that also provides the needed structural strength required by a frame. An example of such a material is a glass infused nylon such as DuPont Zytel®.

Figure 4:
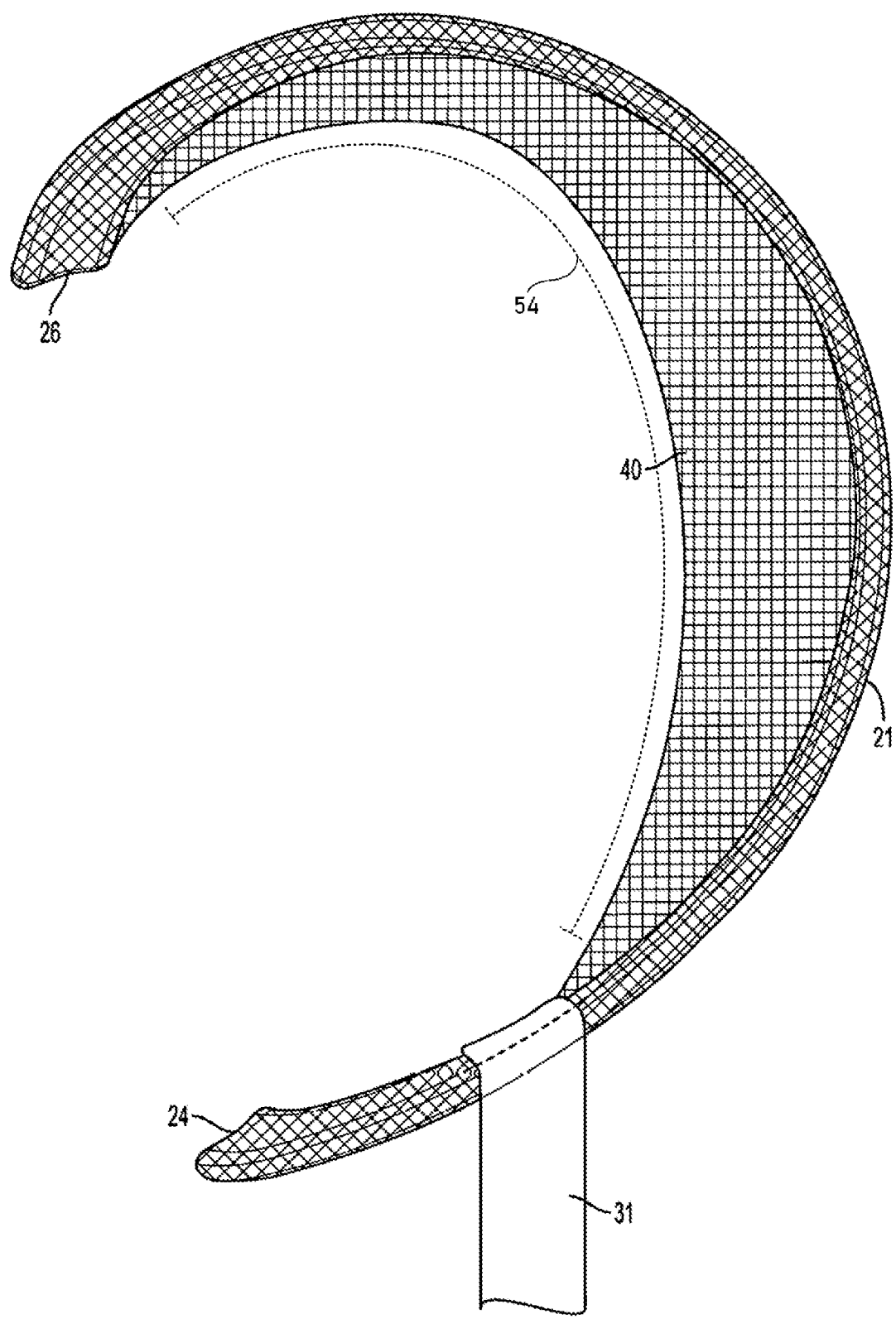
FIG. 4 is side view of an embodiment of a neck support apparatus.
Figure 5:
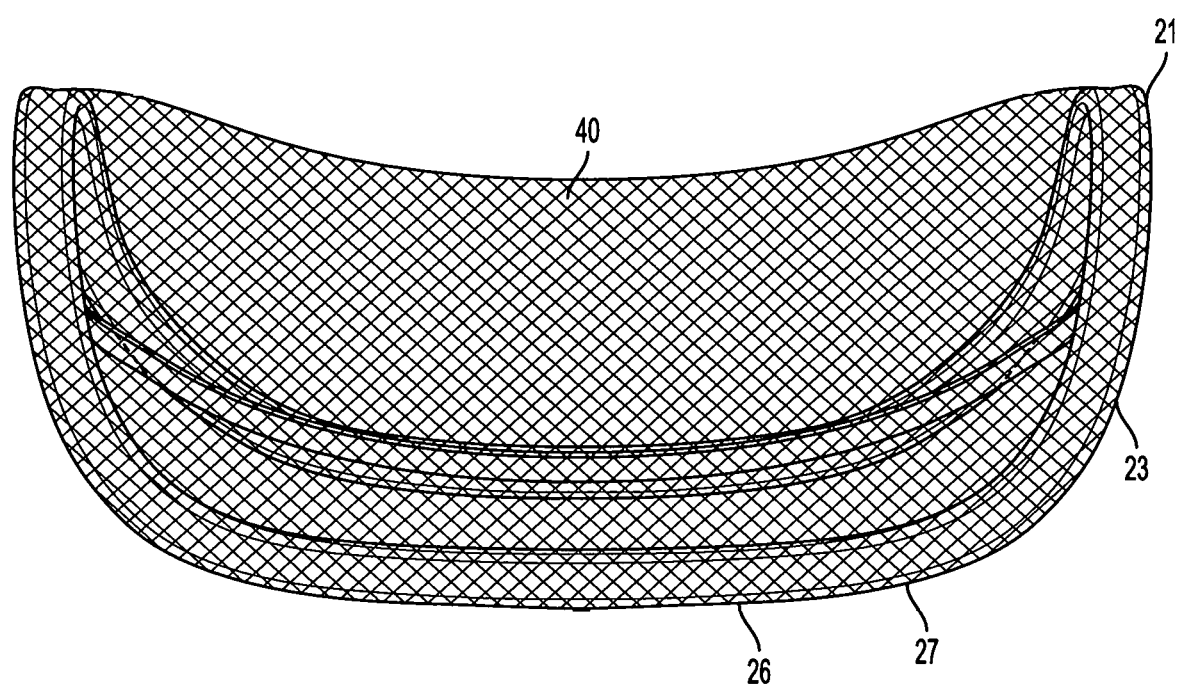
FIG. 5 is a top view of an embodiment of a neck support apparatus.

FIG. 4 is side view of an embodiment of a neck support apparatus 10. In FIG. 4, the shape of risers 21, lower transverse section 24, and upper transverse section 26 and the tension in panel of flexible material 40 cause flexible panel 40 to pull back toward lower transverse section 24 and upper transverse section 26 between risers 21. As a result, the flexible panel exhibits a second curvature 54 that is different from the first curvature 52. FIG. 5 is a top view of an embodiment of a neck support apparatus 10. In FIG. 5, flexible panel 40 curves back toward the upper and lower transverse sections in between risers 21. In the embodiments shown in FIGS. 4 and 5, the interaction of the shape of the frame and the tension in flexible panel 40 results in a compound curvature in the surface presented by flexible panel 40. Other figures show the curvature of the surface presented by flexible panel 40 as well. For example, referring back to the embodiment of head and neck support apparatus shown in FIG. 2, the compound curvature of flexible panel 40 may also be seen in that embodiment. As can be seen in the following figures showing the apparatus in relationship to a wearer of the apparatus, the curvature in the up and down direction accommodates a neck arching backward, while the side to side curvature surrounds the wearer's neck and results in support in the full range of motion of the neck.

Figure 6:
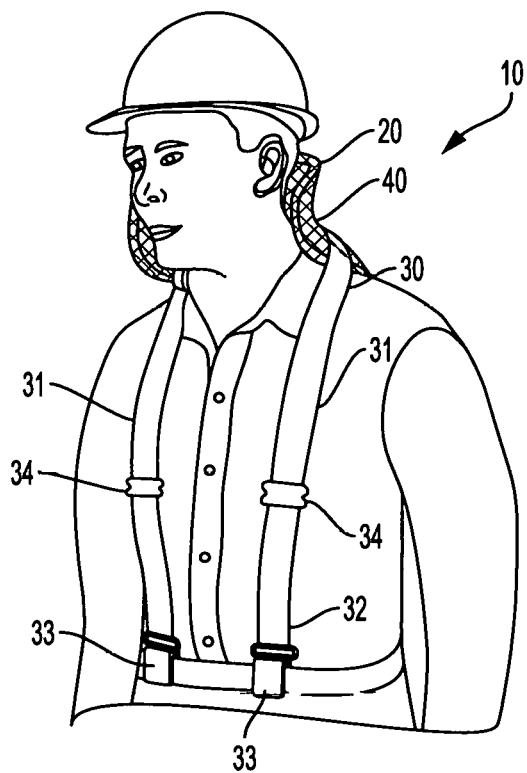
FIG. 6 is a right perspective view of an embodiment of a neck support apparatus being worn.
Figure 7:
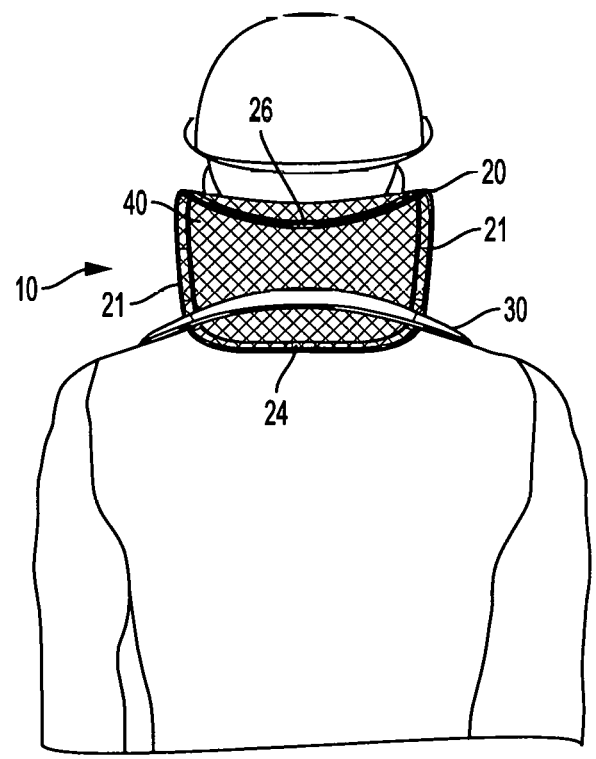
FIG. 7 is a back view of an embodiment of a neck support apparatus being worn.
Figure 8:
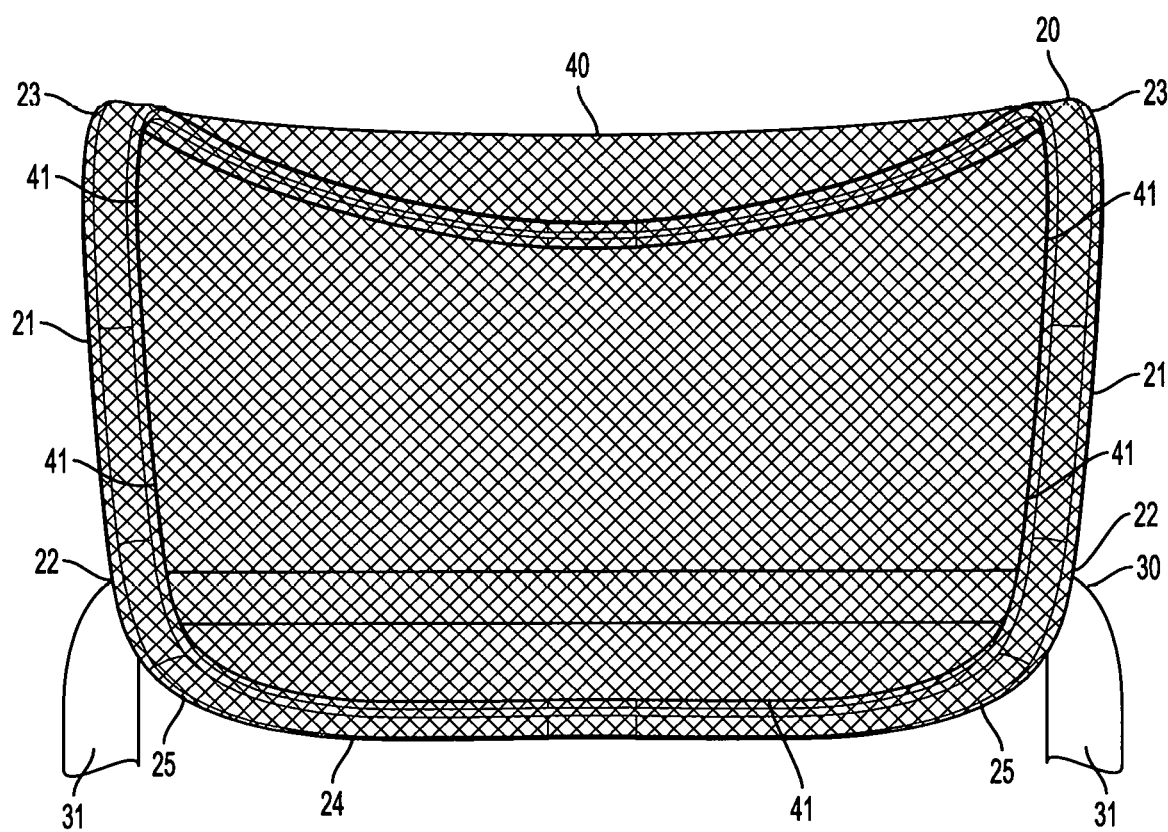
FIG. 8 is a front view of the frame portion of a neck support apparatus.
Figure 9:
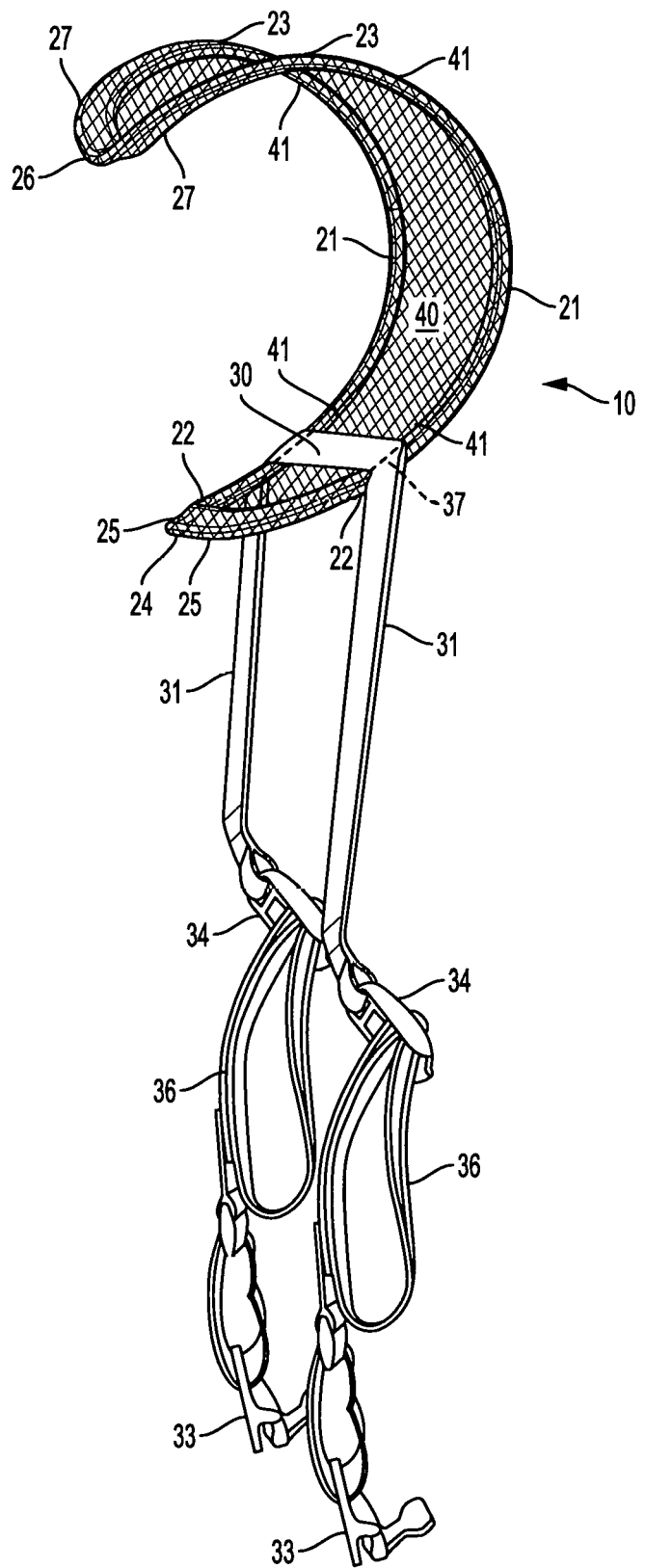
FIG. 9 is a side perspective view of an embodiment of a neck support apparatus.

FIGS. 6 and 7 show an embodiment of neck supporting apparatus 10 in relation to a user of the device. FIG. 6 is a right perspective view of an embodiment of a neck support apparatus 10 being worn by a user. FIG. 7 is a back view of an embodiment of a neck support apparatus 10 being worn. FIG. 8 is a front view of frame 20 and flexible panel 40 portion of a neck support apparatus 10 and provides an enlarged view of frame 20, flexible panel 40, and a portion of harness 30. FIG. 9 is a side perspective view of an embodiment of a neck support apparatus 10 and provides additional illustration of how frame 20 shapes panel 40.

FIGS. 6-9 show embodiments of neck support apparatus 10 wherein frame 20 is a closed hoop, each having two risers 21 at each end of their frames 20 with a lower transverse section 24 and an upper transverse section 26 maintaining risers 21 spaced apart. Each of the sections of frame 20 have a curvature to them and in the various embodiments, the several curvatures of the different sections of frame 20 contribute to the shape of the surface presented by flexible panel 40 before it bears any load. The curves of various sections are not necessarily circular, but may have changing centers of curvature as the section is traversed from one end to the other. The curvatures of the various sections may be compound curves. Which is to say, the several sections may not be planar, but may be curved in 3 dimensions. Additionally, cross sections of the various sections of frame 20 may also twist as a section is traversed from one end to the other. Some sections of frame 20 may have a broad, nearly flat, surface, particularly where frame 20 contacts a wearer. All of these characteristics for frame 20 contribute to the shape of the surface presented by flexible panel 40. The shape of the surface presented by flexible panel 40 is also affected by where and how flexible panel 40 is attached to frame 20.

Still referring to FIGS. 6-9, the curvatures of the different sections of frame 20 will be discussed in relation to the wearer, and how the curvatures shape flexible panel 40. Lower transverse section 24 presents a central curve having a pronounced first curvature opened toward the neck of the wearer. Lower transverse section 24 may have a less noticeable second curvature that assists frame 20 to conform to the back of a wearer. At each end 25 of the central curve of lower transverse section 24, frame 20 is directed forward and upward and ends 25 of lower transverse section 24 blend into lower ends 22 of risers 21. Risers 21 have a first highly pronounced curvature opened away from the wearer, which causes risers 21 to curve back from the wearer. Risers 21 may have a second curvature that affects the space between upper ends 23 of risers 21. This curvature could be inward to bring upper ends 23 closer together, or it could be outward to increase the space between upper ends 23. The cross section of risers 21 could also twist as risers 21 are traversed along their length to assist or accentuate the effect of the curvatures of risers 21. At their upper ends 23, risers 21 curve toward each other and blend into ends 27 of upper transverse section 26. Upper transverse section 26 has a first pronounced curvature opened toward the wearer's neck and a less pronounced second curvature downward toward the wearers back. At each end 27, upper transverse section 26 curves forward to blend into upper ends 23 of risers 21.

Having discussed frame 20, the resulting surface presented by flexible panel 40 can be seen in FIGS. 8 and 9 in particular. In the embodiments of FIGS. 6-9, flexible panel 40 initially has a perimeter and that entire perimeter is fixed to frame 20 around the entire hoop of frame 20 in a moderately taut unloaded state. The several curvatures of the several sections of frame 20 determine the shape of the surface presented by flexible panel 40. The first pronounced curvatures of risers 21 produce a cylindrical surface characteristic running from end to end of frame 20, while the curvatures of lower transverse section 24 and upper transverse section 26 produce a reduced radius of curvature in the central region of the surface presented by flexible panel 40. As a result, flexible panel 40 presents a generally cylindrical surface from end to end, smoothly decreasing from one end to its smallest radius in the central region and smoothly increasing to the other end from the central region back to the larger radius at the other end. This results in a smooth cradling surface in flexible panel 40 before it is loaded by the head of a wearer. From end to end, the surface of flexible panel 40 curves around the neck and head of the wearer. In FIG. 9, fastening 37 maintains strap 30 attached to frame 20.

As seen in FIG. 7, harness 30 maintains frame 20 and flexible panel 40 in contact with the upper back of a wearer of neck support apparatus 10. FIG. 6 shows neck support apparatus 10 in position before undergoing loading. Flexible panel 40 curves around the neck and head of a wearer. In the embodiment of FIG. 9, straps 31 each have an elastic section 36, which maintain frame 20 and flexible panel 40 in place without an overly rigid tension in straps 31.

Figure 10:
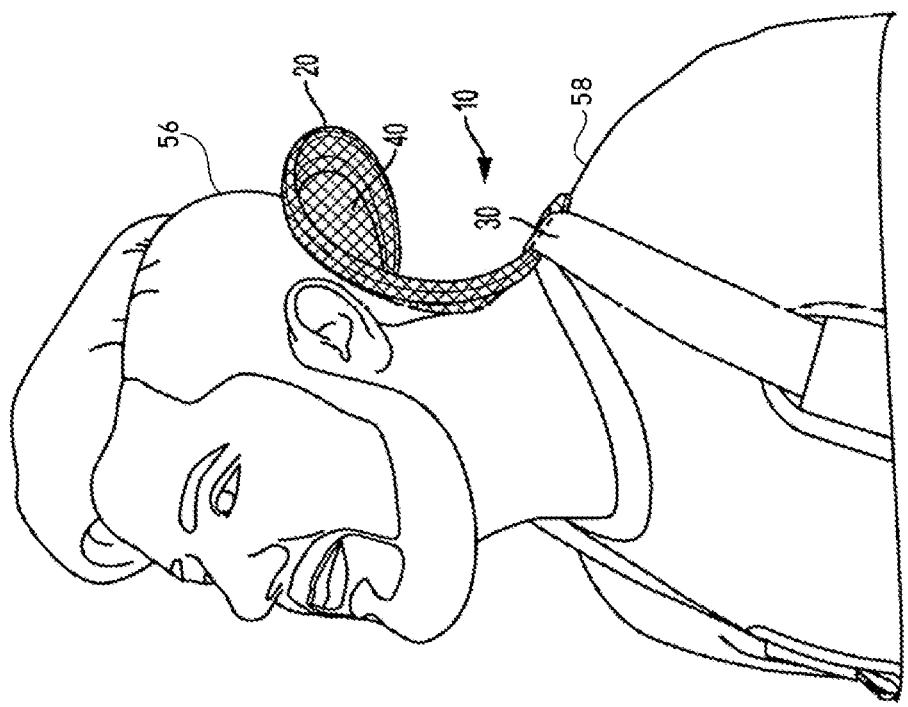
FIG. 10 is a right perspective view of an embodiment of a neck support apparatus being worn while the wearer's head is tilted straight back.

FIG. 10 is a right perspective view of an embodiment of a neck support apparatus 10 being worn while the wearer's head 56 is tilted straight back into flexible panel 40. The wearer's head tilts back onto the reduced central region of the surface presented by flexible panel 40. The reduced radius of curvature in the central section conforms to the arc of the bent neck and head 56 of the wearer and receives and supports the wearer's neck and head 56. The resilience of frame 20, initial tautness of flexible panel 40, and the elastic characteristics of flexible panel 40 will influence how flexible panel 40 conforms to the head of a wearer and supports the neck of a wearer as the head is tilted back into flexible panel 40.

Figure 11:
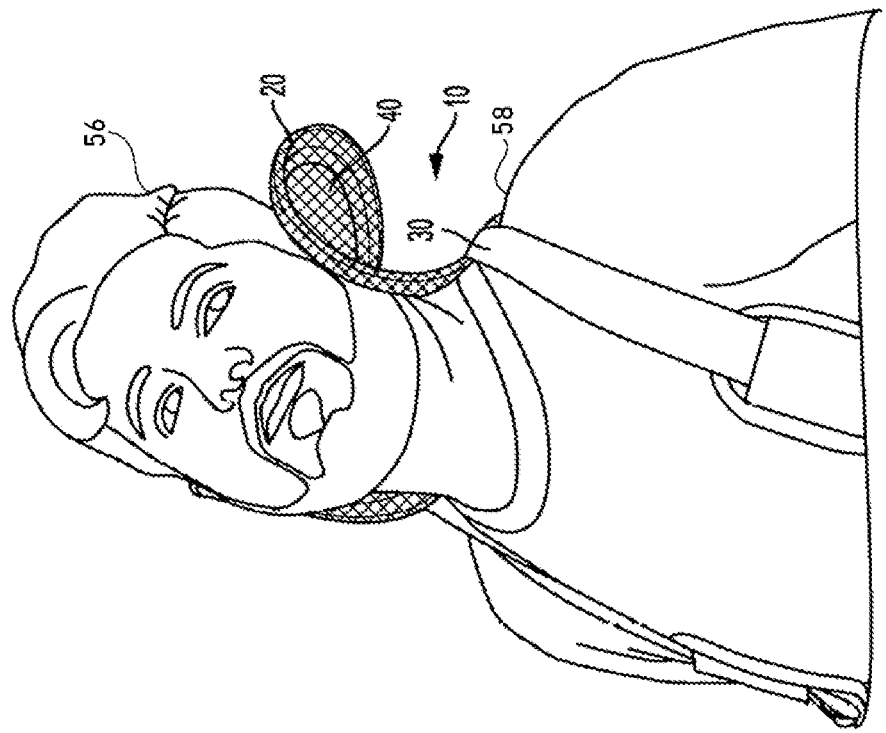
FIG. 11 is a right perspective view of an embodiment of a neck support apparatus being worn while the wearer's head is tilted back and turned to a side.

FIG. 11 is a right perspective view of an embodiment of a neck support apparatus 10 being worn while the wearer's head is tilted back and turned to a side. The curvature of flexible panel 40 allows freedom of motion of the head while still providing support and without resistance from neck support apparatus 40. The wearer's head can roll along the curved surface of flexible panel 40 and receive support through the motion. The wearer does not have to overcome resistance from the apparatus to turn the head while tilted back. As when the head is tilted straight back, the resilience of frame 20, initial tautness of flexible panel 40, and the elastic characteristics of flexible panel 40 will influence how flexible panel 40 conforms to the head of a wearer and supports the neck of a wearer as the head is tilted back into flexible panel 40 and turned.

Figure 12:
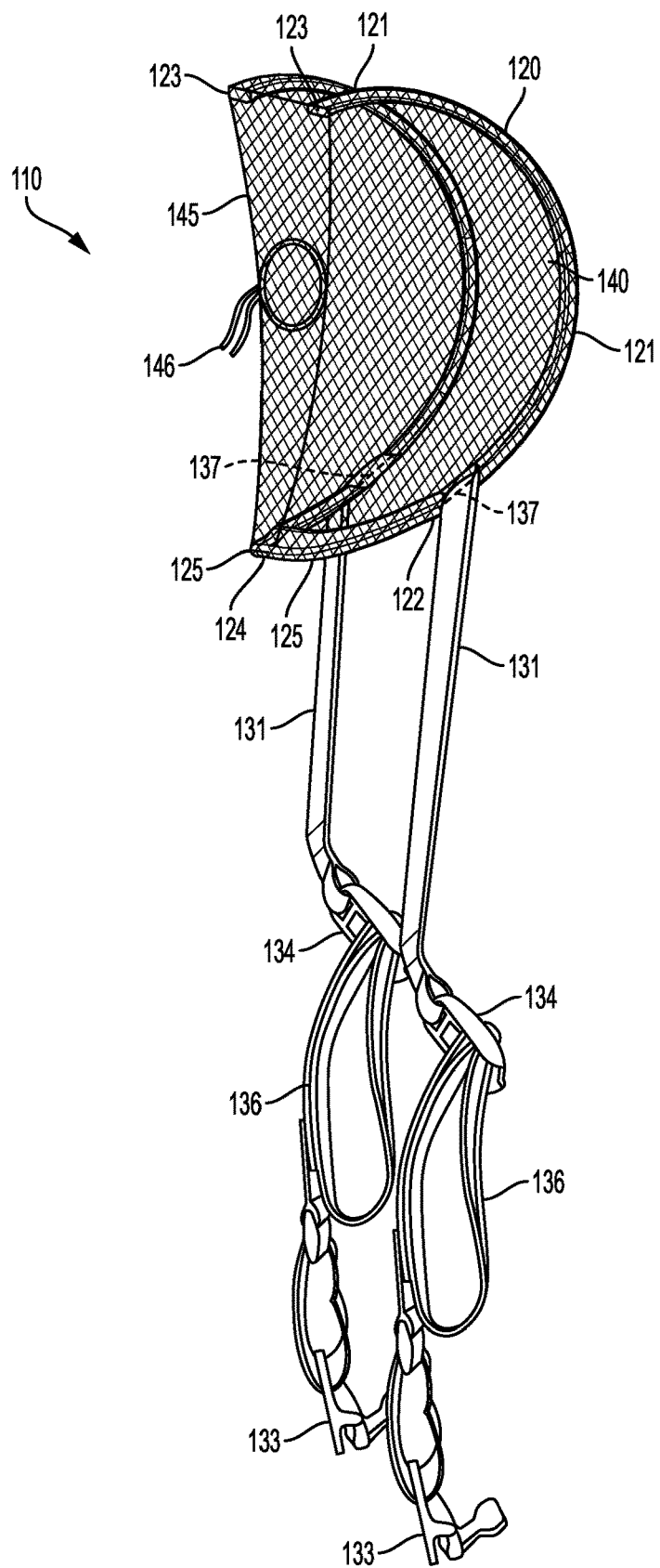
FIG. 12 is a side perspective view of an embodiment of a neck support apparatus with an open hoop frame.

FIG. 12 is a side perspective view of an embodiment of a neck support apparatus 110 with an open hoop frame 120. In the embodiment shown in FIG. 12, frame 120 has a pair of risers 121 spaced a distance apart from each other and running essentially vertically. A lower transverse section 124 has two ends 125, each of which join a respective lower end 122 of a riser 121. In the embodiment of FIG. 12, lower transverse section 124 maintains risers 121 spaced apart. Open hoop frame 120 terminates at upper ends 123 of risers 121, leaving frame 120 open across the top. Upper ends 123 of risers 121 maintain their separation through the resilience of frame 120.

In the embodiment of neck support apparatus 110 of FIG. 12, sleeve 145 envelopes frame 120. Sleeve 145 is comprised of a flexible material. Sleeve 145 presents several surfaces defined by the elastic characteristics of its flexible material, the contours of open hoop frame 120, and the tautness of sleeve 145. One of the surfaces presented by sleeve 145 is flexible panel 140. Flexible panel 140 is the surface of sleeve 145 that faces the neck and head of the wearer and supports the neck and head when the head of the wearer is tilted back into the flexible panel 140. String 146 closes sleeve 145 about frame 120.

In the embodiment of neck support apparatus 110 of FIG. 12, frame 120, sleeve 145, and flexible panel 140 are maintained in position by straps 131. In FIG. 12, fixed ends 137 of straps 131 attach to frame 120. At the free ends of straps 131, clamps 133 provide a means of connecting neck support apparatus to the clothing of the user of the device. Other connectors could be used instead of clamps 133. Buckles 134 provide adjustment to the length of straps 131 while elastic sections 136 allow straps 131 to have tension without being rigid.

Figure 13:
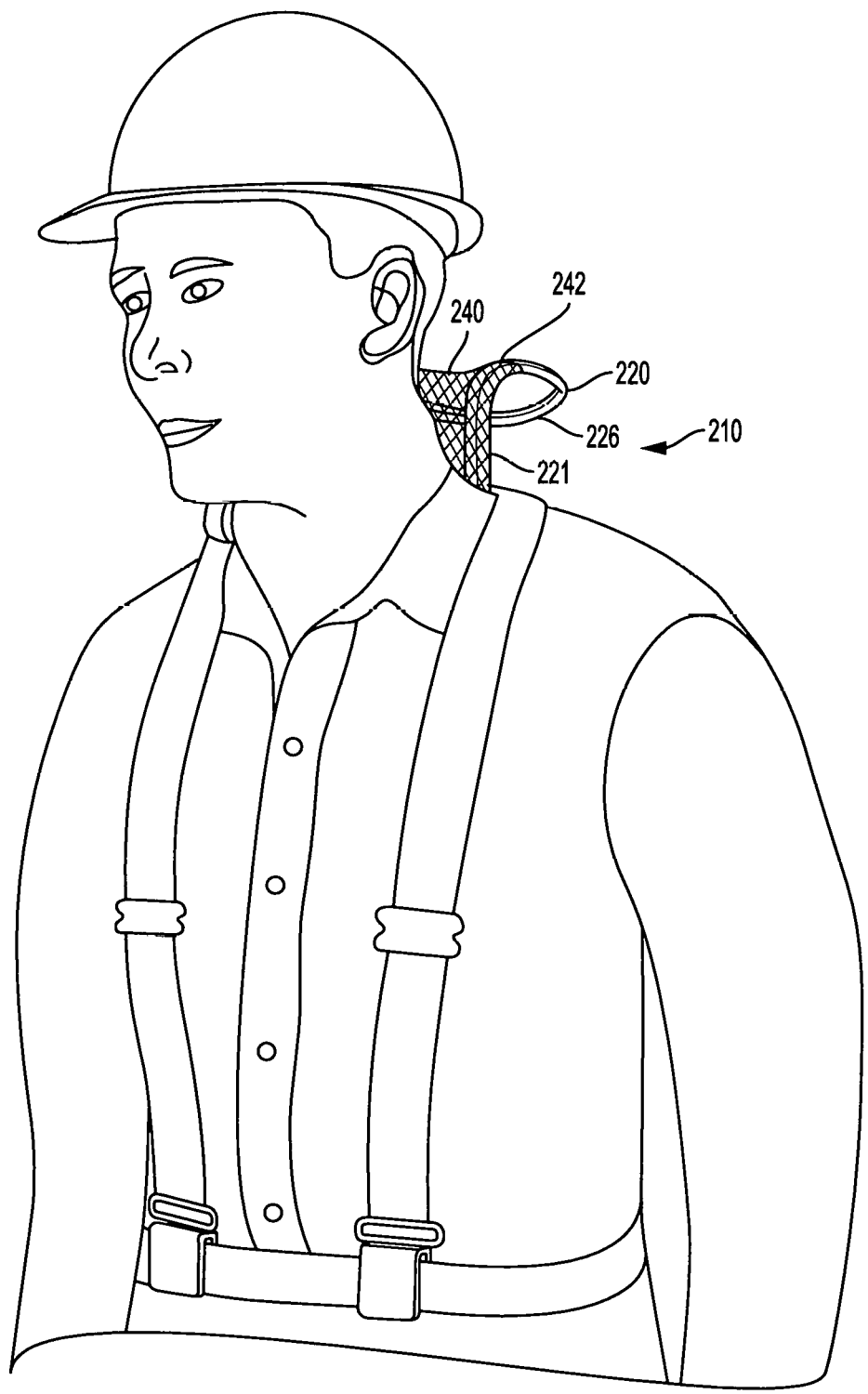
FIG. 13 is a front perspective view of an embodiment of a neck support apparatus with a shortened flexible panel.

FIG. 13 is a front perspective view of an embodiment of a neck support apparatus 210 with a shortened flexible panel 240. In the embodiment of FIG. 13, flexible panel 240 is attached to riser 221 along a shorted edge of the perimeter of flexible panel 240. This leaves an opening between flexible panel 240 and frame 220 along upper transverse section 226.

Figure 14:
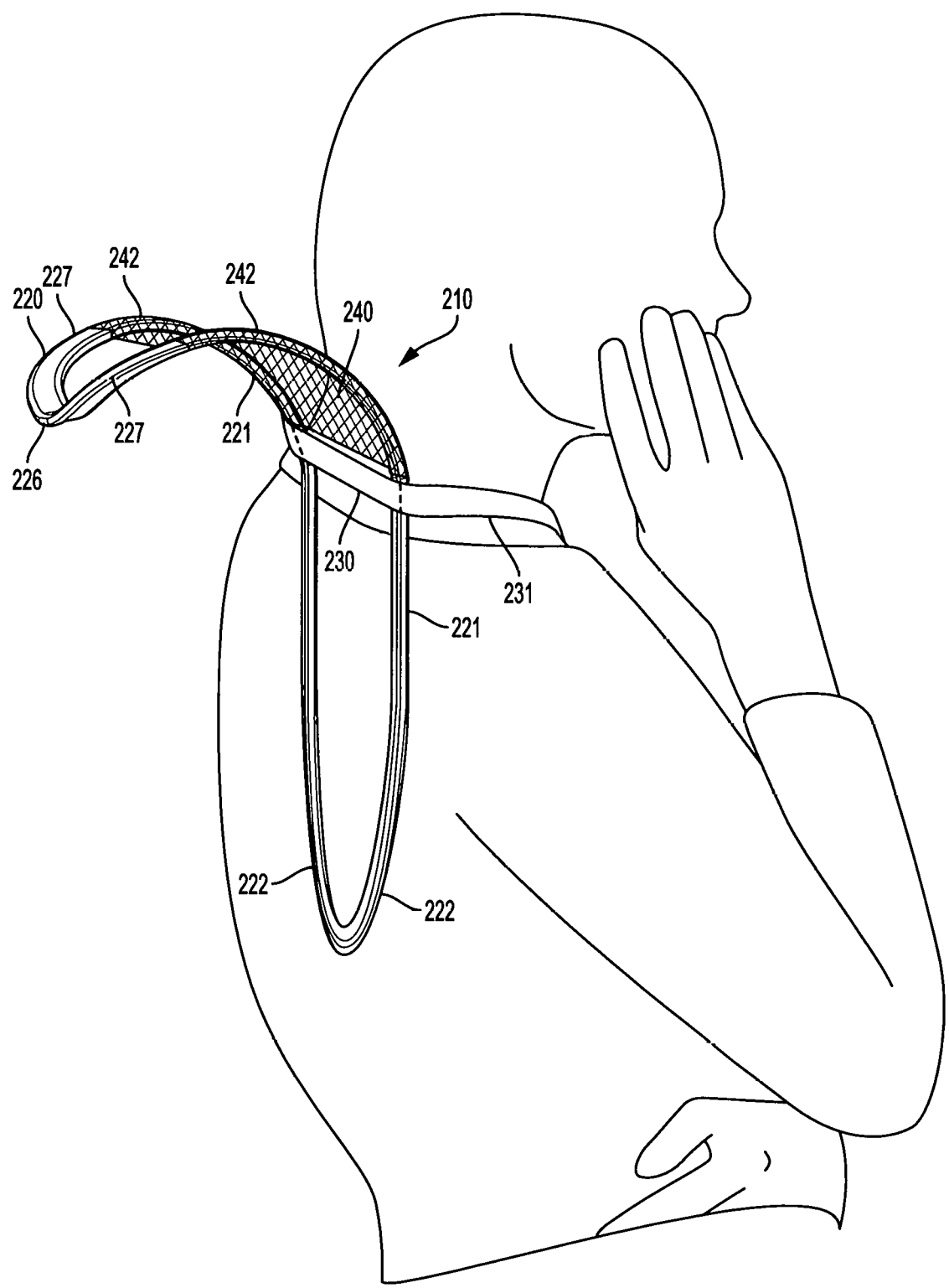
FIG. 14 is a rear perspective view of an embodiment of a neck support apparatus with a long frame and shortened flexible panel.

FIG. 14 is a rear perspective view of an embodiment of a neck support apparatus 210 with a long frame 220 and shortened flexible panel 240. In the embodiment of FIG. 14, frame 220 comprises two risers 221 joined directly to each other at their lower ends 222. Risers 221 spread further apart as they rise up the back until they curve away from the head and neck of the wearer and then back toward each other at their upper ends 223. At their upper ends 223, risers 221 blend into upper transverse section 226 at ends 227 of upper transverse section 226. Upper transverse section 226 maintains risers 221 spaced apart.

In the embodiment of neck support apparatus 210 of FIG. 14, flexible panel 240 spans between risers 221. Flexible panel 240 is comprised of a flexible material such as cloth, mesh, plastic, or any equivalent flexible material. Flexible panel 240 has a perimeter having at least two opposing edges 242. Flexible panel 240 is attached along each opposing edge 242 to a respective riser 221, and flexible panel 240 spans between risers 221. Other than opposing edges 242, the balance of the perimeter of panel 240 is unattached to frame 220. The shape of the supporting surface presented to a wearer's head and neck by flexible panel 240 will be determined by the curvature of risers 221, the material of flexible panel 240, the initial tautness of flexible panel 240, the length of edges 242, and other factors as well. Additionally, in the embodiment of FIG. 14, harness 230 comprises two straps 231 extending from it, one of which is visible in FIG. 14. Straps 231 attach to the clothing of the wearer and may be adjustable in length. This provides varying degrees of tension which can also vary the response of panel 240 and frame 220.

It is to be understood that the embodiments and arrangements set forth herein are not limited in their application to the details of construction and arrangement of the components set forth in the description and illustrated in the drawings. Rather, the description and the drawings provide examples of the embodiments envisioned, but the invention is not limited to the specific embodiments. The embodiments disclosed herein are further capable of other embodiments and of being practiced and carried out in various ways, including various combinations and sub-combinations that may not have been explicitly disclosed. Also, it is to be understood that the phraseology and terminology employed herein are for the purposes of description and should not be regarded as limiting the claims Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the invention be regarded as including such equivalent constructions.

I claim:

1. A neck support apparatus, comprising:
   a curved unitary hoop that includes a pair of risers and a pair of transverse sections that connect the pair of risers,
      wherein each riser of the pair of risers includes an upper portion and a lower portion, such that, when a user is wearing the curved unitary hoop:
         each upper portion is configured to be more proximal to a head of the user than a shoulder of the user, and
         each lower portion is configured to be more proximal to the shoulder of the user than the head of the user;
      wherein each upper portion of each riser includes a section that is configured to curve towards a lower transverse section of the pair of transverse sections and towards the shoulder of the user that is wearing the curved unitary hoop;
   a fabric that spans between the pair of risers and contacts a perimeter of the curved unitary hoop,
      wherein a curvature of the curved unitary hoop is configured to cause the fabric to exhibit a first curvature between the pair of transverse sections, and a second curvature, that is different from the first curvature, between the pair of risers; and
   a harness that extends between the pair of risers of the curved unitary hoop when the harness is connected to the curved unitary hoop,
      wherein the harness comprises free ends with connectors that are configured to connect to a portion of user clothing that is more proximal to the shoulder of the user than the head of the user, and
      wherein the harness extends across the lower portion of each riser and the fabric, at a region of the fabric that is more proximal to the lower transverse section than an upper transverse section of the pair of transverse sections.

2. The neck support apparatus of claim 1, wherein the harness further comprises two elastic sections between the free ends.

3. The neck support apparatus of claim 1, wherein the fabric is made from a mesh material that is arc-rated.

4. The neck support apparatus of claim 3, wherein the curved unitary hoop and the fabric are made from flame retardant materials.

5. The neck support apparatus of claim 4, wherein the curved unitary hoop is made from a glass infused nylon.

6. The neck support apparatus of claim 1, wherein the first curvature exhibited by the fabric is a compound curvature.

7. A neck support apparatus, comprising:
   a curved unitary hoop that includes a pair of risers and a pair of transverse sections that connect the pair of risers,
      wherein each riser of the pair of risers includes an upper portion and a lower portion, such that, when a user is wearing the curved unitary hoop:
         each upper portion is configured to be more proximal to a head of the user than a shoulder of the user, and
         each lower portion is configured to be more proximal to the shoulder of the user than the head of the user;
      wherein each upper portion of each riser includes a section that is configured to curve away from the head of the user and is configured to curve towards a lower transverse section of the pair of transverse sections and towards the should of the user that is wearing the curved unitary hoop;
   a fabric that spans between the pair of risers and contacts a perimeter of the curved unitary hoop,
      wherein a curvature of the curved unitary hoop is configured to cause the fabric to exhibit a first curvature between the pair of transverse sections, and a second curvature, that curves differently from the first curvature, between the pair of risers; and
   a harness that extends between the pair of risers of the curved unitary hoop when the harness is connected to the curved unitary hoop,
      wherein the harness comprises free ends with connectors that are configured to connect to a portion of user clothing that is more proximal to the shoulder of the user than the head of the user, and wherein the harness extends across the lower portion of each riser and the fabric, at a region of the fabric that is more proximal to the lower transverse section than an upper transverse section of the pair of transverse sections.

8. The neck support apparatus of claim 7, wherein the curved unitary hoop is made from a glass infused nylon.

9. The neck support apparatus of claim 7, wherein the fabric is made from a flame retardant material.

\* \* \* \* \*